US009817944B2

(12) United States Patent
Kural

(10) Patent No.: US 9,817,944 B2
(45) Date of Patent: Nov. 14, 2017

(54) SYSTEMS AND METHODS FOR ANALYZING SEQUENCE DATA

(71) Applicant: Seven Bridges Genomics Inc., Cambridge, MA (US)

(72) Inventor: Deniz Kural, Somerville, MA (US)

(73) Assignee: Seven Bridges Genomics Inc., Cambridge, MA (US)

( * ) Notice: Subject to any disclaimer, the term of this patent is extended or adjusted under 35 U.S.C. 154(b) by 817 days.

(21) Appl. No.: 14/177,958

(22) Filed: Feb. 11, 2014

(65) Prior Publication Data
US 2015/0227685 A1 Aug. 13, 2015

(51) Int. Cl.
G01N 33/48 (2006.01)
G06F 19/22 (2011.01)
G06F 19/26 (2011.01)
C12Q 1/68 (2006.01)

(52) U.S. Cl.
CPC .......... *G06F 19/22* (2013.01); *C12Q 1/6869* (2013.01); *G06F 19/26* (2013.01); *C12Q 2521/301* (2013.01)

(58) Field of Classification Search
CPC ...................................................... G06F 19/22
USPC ................................................................ 702/19
See application file for complete search history.

(56) References Cited

U.S. PATENT DOCUMENTS

| | | | |
|---|---|---|---|
| 5,583,024 A | 12/1996 | McElroy et al. | |
| 5,674,713 A | 10/1997 | McElroy et al. | |
| 5,700,673 A | 12/1997 | McElroy et al. | |
| 5,701,256 A | 12/1997 | Marr et al. | |
| 6,210,891 B1 | 4/2001 | Nyren et al. | |
| 6,306,597 B1 | 10/2001 | Macevicz | |
| 6,818,395 B1 | 11/2004 | Quake et al. | |
| 6,828,100 B1 | 12/2004 | Ronaghi | |
| 6,833,246 B2 | 12/2004 | Balasubramanian | |
| 6,890,763 B2 | 5/2005 | Jackowski et al. | |
| 6,911,345 B2 | 6/2005 | Quake et al. | |
| 6,925,389 B2 | 8/2005 | Hitt et al. | |
| 6,989,100 B2 | 1/2006 | Norton | |
| 7,169,560 B2 | 1/2007 | Lapidus et al. | |
| 7,232,656 B2 | 6/2007 | Balasubramanian et al. | |
| 7,282,337 B1 | 10/2007 | Harris | |
| 7,598,035 B2 | 10/2009 | Macevicz | |
| 7,620,800 B2 | 11/2009 | Huppenthal et al. | |
| 7,835,871 B2 | 11/2010 | Kain et al. | |
| 7,917,302 B2 | 3/2011 | Rognes | |
| 7,960,120 B2 | 6/2011 | Rigatti et al. | |
| 8,146,099 B2 | 3/2012 | Tkatch et al. | |
| 8,370,079 B2 | 2/2013 | Sorenson et al. | |
| 9,063,914 B2 | 6/2015 | Kural et al. | |
| 2002/0164629 A1 | 11/2002 | Quake et al. | |
| 2006/0024681 A1 | 2/2006 | Smith et al. | |
| 2006/0195269 A1 | 8/2006 | Yeatman et al. | |
| 2006/0292611 A1 | 12/2006 | Berka et al. | |
| 2007/0114362 A1 | 5/2007 | Feng et al. | |
| 2007/0166707 A1 | 7/2007 | Schadt et al. | |
| 2008/0251711 A1 | 10/2008 | Reilly | |
| 2008/0294403 A1 | 11/2008 | Zhu et al. | |
| 2009/0026082 A1 | 1/2009 | Rothberg et al. | |
| 2009/0119313 A1 | 5/2009 | Pearce | |
| 2009/0127589 A1 | 5/2009 | Rothberg et al. | |
| 2009/0191565 A1 | 7/2009 | Lapidus et al. | |
| 2009/0300781 A1 | 12/2009 | Bancroft et al. | |
| 2010/0010992 A1 | 1/2010 | Morris | |
| 2010/0035252 A1 | 2/2010 | Rothberg et al. | |
| 2010/0137143 A1 | 6/2010 | Rothberg et al. | |
| 2010/0188073 A1 | 7/2010 | Rothberg et al. | |
| 2010/0197507 A1 | 8/2010 | Rothberg et al. | |
| 2010/0282617 A1 | 11/2010 | Rothberg et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2011/0009278 A1 | 1/2011 | Kain et al. | |
| 2011/0207135 A1 | 8/2011 | Faham et al. | |
| 2012/0030566 A1 | 2/2012 | Victor | |
| 2012/0040851 A1 | 2/2012 | Lieberman et al. | |

(Continued)

FOREIGN PATENT DOCUMENTS

WO 2007/086935 A2 8/2007
WO 2012/142531 A2 10/2012

OTHER PUBLICATIONS

Homer et al. "Improved Variant Discovery Through Local Realignment of Short-Read Next-Generation Sequencing Data Using SRMA" Genome Biology (2010) vol. 11, pp. R:99.*
Grasso, 2004, Combining partial order alignment and progressive multiple sequence alignment increases alignment speed and scalability to very large alignment problems, Bioinformatics 20(10):1546-1556.
Bertone et al., 2004, Global identification of human transcribed sequences with genome tiling arrays, Science 306:2242-2246.
Black, 2005, A simple answer for a splicing conundrum, PNAS 102:4927-8.
Carrington et al., 1985, Polypeptide ligation occurs during post-translational modification of concanavalin A, Nature 313:64-67.
Chang et al., 2005, The application of alternative splicing graphs in quantitative analysis of alternative splicing form from EST database, Int J. Comp. Appl. Tech 22(1): 14.
Delcher et al., 1999, Alignment of whole genomes, Nucleic Acids Research, 27(11):2369-2376.

(Continued)

Primary Examiner — Jerry Lin
(74) Attorney, Agent, or Firm — Kip L. Bodi

(57) ABSTRACT

The invention provides methods for comparing one set of genetic sequences to another without discarding any information within either set. A set of genetic sequences is represented using a directed acyclic graph (DAG) avoiding any unwarranted reduction to a linear data structure. The invention provides a way to align one sequence DAG to another to produce an alignment that can itself be stored as a DAG. DAG-to-DAG alignment is a natural choice wherever a set of genomic information consisting of more than one string needs to be compared to any non-linear reference. For example, a subpopulation DAG could be compared to a population DAG in order to compare the genetic features of that subpopulation to those of the population.

19 Claims, 10 Drawing Sheets

(56) References Cited

U.S. PATENT DOCUMENTS

| | | |
|---|---|---|
| 2012/0041727 A1 | 2/2012 | Mishra et al. |
| 2012/0239706 A1 | 9/2012 | Steinfadt |
| 2013/0029879 A1 | 1/2013 | Shetty et al. |
| 2013/0035904 A1 | 2/2013 | Kuhn |
| 2013/0124100 A1 | 5/2013 | Drmanac et al. |

OTHER PUBLICATIONS

Florea et al., 2005, Gene and alternative splicing annotation with AIR, Genome Research 15:54-66.
Garber et al., 2011, Computational methods for transcriptome annotation and quantification using RNA-Seq, Nat Meth 8(6):469-477.
Harrow et al., 2012, Gencode: The reference human genome annotation for The Encode Project, Genome Res 22:1760-1774.
Heber et al., 2002, Splicing graphs and EST assembly problems, Bioinformatics 18 Suppl:181-188.
Kim et al., 2005, ECgene: Genome-based EST clustering and gene modeling for alternative splicing, Genome Research 15:566-576.
Kurtz et al., 2004, Versatile and open software for comparing large genomes, Genome Biology, 5:R12.
Langmead et al., 2009, Ultrafast and memory-efficient alignment of short DNA sequences to the human genome, Genome Biology 10:R25.
Lee et al., 2005, Bioinformatics analysis of alternative splicing, Brief Bioinf 6(I):23-33.
LeGault et al., 2013, Inference of alternative splicing from RNA-Seq data with probabilistic splice graphs, Bioinformatics 29(18):2300-2310.
Leipzig et al., 2004, The alternative splicing gallery (ASG): Bridging the gap between genome and transcriptome, Nucleic Acids Res., 23(13):3977-3983.
Li et al., 2008, SOAP: short oligonucleotide alignment program, Bioinformatics 24(5):713-14.
Li et al., 2009, SOAP2: an improved ultrafast tool for short read alignment, Bioinformatics 25(15): 1966-67.
Lindgreen, 2012, AdapterRemoval: easy cleaning of next-generation sequence reads, BMC Res Notes 5:337.
Nakao et al., 2005, Large-scale analysis of human alternative protein isoforms: pattern classification and correlation with subcellular localization signals, Nucl Ac Res 33(8):2355-2363.
Pearson et al., 1988, Improved tools for biological sequence comparison, PNAS 85(8):2444-8.
Shao et al., 2006, Bioinformatic analysis of exon repetition, exon scrambling and trans-splicing in humans, Bioinformatics 22:692-698.
Slater et al., 2005, Automated generation of heuristics for biological sequence comparison, BMC Bioinformatics 6:31.
Wang et al., 2009, RNA-Seq: a revolutionary tool for transcriptomics, Nat Rev Genet 10(I):57-63.
Xing et al., 2006, An expectation-maximization algorithm for probabilistic reconstructions of full-length isoforms from splice graphs, Nucleic Acids Research, 34:3150-3160.
Grabherr et al., 2011, Full-length transcriptome assembly from RNA-Seq data without a reference genome, Nature Biotechnology 29(7):644-654.
Costa et al., 2010, Uncovering the Complexity of Transcriptomes with RNA-Seq, Journal of Biomedicine and Biotechnology Article ID 853916:1-19.
LeGault et al., 2010, Learning Probalistic Splice Graphs from RNA-Seq data, pages.cs.wisc.edu/~legault/cs760_writeup.pdf; retrieved from the internet on Apr. 6, 2014.
Trapnell et al., 2010, Transcript assembly and quantification by RNA-Seq reveals unannotated trancripts and isoform switching during cell differentiation, Nature Biotechnology 28(5):511-515.
Guttman et al., 2010, Ab initio reconstruction of cell type-specific transcriptomes in mouse reveals the conserved multi-exonic structure of lincRNAs, Nature Biotechnology 28(5):503-510.
NIH Public Access Author Manuscript, Trapnell et al., 2010, Transcript assembly and abundance estimation from RNA-Seq reveals thousands of new transcripts and swtiching among isoforms, NIH-PA Author Manuscript.
NIH Public Access Author Manuscript, Guttman et al., 2010, Ab initio reconstruction of transcriptomes of pluripotent and lineage committed cells reveals gene structures of thousands of lincRNAs, NIH-PA Author Manuscript.
Kent, 2002, BLAT—The Blast-Like Alignment Tool, Genome Research 4:656-664.
Lam et al., 2008, Compressed indexing and local alignment of DNA, Bioinformatics 24(6):791-97.
Altschul et al., Optimal Sequence Alignment Using Affine Gap Costs, Bulletin of Mathematical Biology vol. 48, No. 5/6, pp. 603-616, 1986.
Chin et al., Nonhybrid, finished microbial genome assemblies from long-read SMRTS sequencing data Nature Methods vol. 10 No. 6 Jun. 2013 pp. 563-571.
Compeauet et al., How to apply de Bruijn graphs to genome assembly, Nature Biotechnology vol. 29 No. 11, pp. 987-991.
Dudley and Butte, A quick guide for developing effective bioinformatics programming skills, PLoS Comput Biol 5(12):e1000589 (2009).
Farrar et al., Striped Smith-Waterman speeds database searches six times over other SIMD implementations, vol. 23 No. 2 2007, pp. 156-161.
Goto, et al., BioRuby: bioinformatics software for the Ruby programming language, Bioinformatics 26(20):2617-2619 (2010).
Gotoh et al., An Improved Algorithm for Matching Biological Sequences, J. Mol. Bid. (1982) 162, 705-708.
Hein et al., A New Method That Simultaneously Aligns and Reconstructs Ancestral Sequences for Any Number of Homologous Sequences, When the Phylogeny is Given. Mol. Biol. E vol. 6(6):649-668. 1989.
Hein et al., A Tree Reconstruction Method That is Economical in the Number of Pairwise Comparisons Used, Mol. Biol. Evol. 6(6):649-668. 1989.
Holland, et al., BioJava: an open-source framework for bioinformatics, Bioinformatics 24(18):2096-2097 (2008).
Huang, Chapter 3: Bio-Sequence Comparison and Alignment, ser. Curr Top Comp Mol Biol. Cambridge, Mass.: The MIT Press, 2002.
International HapMap Consortium, 2005, A haplotype map of the human genome. Nature 437:1299-1320.
LaFramboise, 2009, Single nucleotide polymorphism arrays: a decade of biological, computational and technological advance, Nucleic Acids Res 37(13):4181-4193.
Larkin et al., 2007, Clustal W and Clustal X version 2.0, Bioinformatics 23(21):2947-2948.
Lee, et al., 2002, Multiples sequence alignment using partial order graphs, Bioinformatics 18(3): 452-464.
Lipman and Pearson, 1985, Rapid and sensitive protein similarity searches, Science 227(4693):1435-41.
Ma et al., Multiple genome alignment based on longest path in directed acyclic graphs. Int. J. Bioinformatics Research and Applications, vol. 6, No. 4, 2010.
Danecek et al., 2011, The variant call format and VCFtools, Bionformatics 27(15):2156-2158.
Li et al., 2010, A survey of sequence alignment algorithms for next-generation sequencing, Briefings in Bionformatics 11(5):473-483.
Schneeberger et al., 2009, Sumaltaneous alignment of short reads against multiple genomes, Genome Biology 10(9):R98.2-R98.12.
International Search Report and Written Opinion dated Dec. 11, 2014, for International Patent Application No. PCT/US14/52065, filed Aug. 21, 2014, (18 pages).
International Search Report and Written Opinion dated Jan. 27, 2015, for International Patent Application No. PCT/US2014/060680, filed Oct. 215, 2014, (11 pages).
International Search Report and Written Opinion dated May 11, 2015, for International Patent Application No. PCT/US2015/015375 with International Filing Date Feb. 11, 2015 (12 pages).
Bao et al., 2013, Branch: boosting RNA-Seq assemblies with partial or related genomic sequences, Bioinformatics.
Bertrand et al., 2009, Genetic map refinement using a comparative genomic approach, J Comp Biol 16(10):1475-1486.

(56) References Cited

OTHER PUBLICATIONS

Manolio, et al., 2010, Genome wide association studies and assessment of the risk of disease, NEJM 363(2):166-76.
Margulies et al., 2005, Genome sequencing in micro-fabricated high-density picotiter reactors, Nature, 437:376-380.
Miller et al., Assembly Algorithms for Next-Generation Sequencing Data, Genomics. Jun. 2010 ; 95(6): 315-327.
Mount et al., Multiple Sequence Alignment, Bioinformatics, 2001, Cold Spring Harbor Laboratory Press, Cold Spring Harbor, New York, pp. 139-204.
Nagalakshmi et al., RNA-Seq: A Method for Comprehensive Transcriptome Analysis, Current Protocols in Molecular Biology 4.11.1.13, Jan. 2010, 13 pages.
Needleman & Wunsch, 1970, A general method applicable to the search for similarities in the amino acid sequence of two proteins, J Mol Biol, 48(3):443-453.
Oshlack et al., From RNA-seq reads to differential expression results. Genoome Bio 2010, 11:220, pp. 1-10.
Pe'er., et al, 2006, Evaluating and improving power in whole-genome association studies using fixed marker sets. Nat. Genet., 38, 663-667.
Potter et al., ASC: An Associative-Computing Paradigm, Computer , 27(11):19-25, 1994.
Quail, et al., 2012, A tale of three next generation sequencing platforms: comparison of Ion Torrent, Pacific Biosciences and Illumina MiSeq sequencers, BMC Genomics 13:341.
Rognes et al., Faster Smith-Waterman database searches with inter-sequence SIMD parallelisation,Bioinformatics 2011, 12:221.
Rognes et al., ParAlign: a parallel sequence alignment algorithm for rapid and sensitive database searches, Nucleic Acids Research, 2001, vol. 29, No. 7 1647-1652.
Rognes et al., Six-fold speed-up of Smith-Waterman sequence database searching using parallel processing on common microprocessors, Bioinformatics vol. 16 No. 8 2000, pp. 699-706.
Rothberg, et al., 2011, An integrated semiconductor device enabling non-optical genome sequencing, Nature 475:348-352.
Saebo et al., Paralign: rapid and sensitive sequence similarity searches powered by parallel computing technology, Nucleic Acids Research, 2005, vol. 33, Web Server issue W535-W539.
Sievers et al., 2011, Fast, scalable generation of high-quality protein multiple sequence alignments using Clustal Omeag, Mol Syst Biol 7:539.
Smith et al., Multiple insert size paired-end sequencing for deconvolution of complex transcriptions, RNA Bio 9:5, 596-609; May 2012.
Smith et al., Identification of Common Molecular Subsequences, J. Mol. Biol. (1981) 147, 195-197.
Soni and Meller, 2007, Progress toward ultrafast DNA sequencing using solid-state nanopores, Clin Chem 53(11):1996-2001.
Stephens, et al,. 2001, A new statistical method for haplotype reconstruction from population data, Am J Hum Genet 68:978-989.
Wang, et al., 2011, Next generation sequencing has lower sequence coverage and poorer SNP-detection capability in the regulatory regions, Scientific Reports 1:55.
Waterman, et al., 1976, Some biological sequence metrics, Adv. in Math. 20(3):367-387.
Wellcome Trust Case Control Consortium, 2007, Genome-wide association study of 14,000 cases of seven common diseases and 3,000 shared controls, Nature 447:661-678.
Wu et al., Fast and SNP-tolerant detection of complex variants and splicing in short reads, Bioinformatics, vol. 26 No. 7 2010, pp. 873-881.
Yu et al., The construction of a tetraploid cotton genome wide comprehensive reference map, Genomics 95 (2010) 230-240.
Yu, et al., A tool for creating and parallelizing bioinformatics pipelines, DOD High Performance Computing Conf., 417-420 (2007).
Hoon, et al., Biopipe: A flexible framework for protocol-based bioinformatics analysis, Genome Research 13(8):1904-1915 (2003).
Altera, 2007, Implementation of the Smith-Waterman algorithm on reconfigurable supercomputing platform, White Paper ver 1.0 (18 pages).
Fitch, 1970, Distinguishing homologous from analogous proteins, Systematic Zoology 19:99-113.
Haas et al., 2004, DAGchainer: a tool for mining segmental genome duplications and synteny, Bioinformatics 20(18):3643-3646.
Lee, 2003, Generating consensus sequences from partial order multiple sequence alignment graphs, Bioinformatics 19(8):999-1008.
Li, et al., 2009, The Sequence Alignment/Map format and SAMtools, Bioinformatics 25(16):2078-9.
Mardis, 2010, The $1,000 genome, the $1,000 analysis?, Genome Med 2:84-85.
Nagarajan & Pop, 2013, Sequence assembly demystified, Nat Rev 14:157-167.
Raphael, 2004, A novel method for multiple alignment of sequences with repeated and shuffled elements, Genome Res 14:2336-2346.
Rodelsperger, 2008, Syntenator: Multiple gene order alignments with a gene-specific scoring function, Alg Mol Biol 3:14.
Schwikowski & Vingron, 2002, Weighted sequence graphs: boosting iterated dynamic programming using locally suboptimal solutions, Disc Appl Mat 127:95-117.
Stewart, et al., 2011, A comprehensive map of mobile element insertion polymorphisms in humans, PLoS Genetics 7(8):1-19.
Yanovsky, et al., 2008, Read mapping algorithms for single molecule sequencing data, Procs of the 8th Int Workshop on Algorithms in Bioinformatics 5251:38-49.
Durham, et al., EGene: a configurable pipeline system for automated sequence analysis, Bioinformatics 21(12):2812-2813 (2005).

* cited by examiner

TTGGATATGGG (SEQ ID NO: 1)
TTGGATCGAATTATGGG (SEQ ID NO: 2)

FIG. 2

GATTACACATGATTACATGACTGACCATTCCAT (SEQ ID NO: 3)
GAGTACAGATTACATGACTGACGGAGCATTACATCT (SEQ ID NO: 4)

GATTACACATGATTACATGACTGACCATTCCAT (SEQ ID NO: 3)
GAGTACA---GATTACATGACTGACGGAGCATTACATCT (SEQ ID NO: 4)

GATTACACATGATTACATGACTGACCATTCCAT (SEQ ID NO: 3)
GAGTACA---GATTACATGACTGACGGAGCATTACATCT (SEQ ID NO: 4)

```
GATTACACATGATTACATGACTGAC-----CATTCCAT (SEQ ID NO: 3)
GAGTACA---GATTACATGACTGACGGAGCATTACATCT (SEQ ID NO: 4)
```

```
GATTACACATGATTACATGACTGAC----CATTCCAT (SEQ ID NO: 3)
GAGTACA---GATTACATGACTGACGGAGCATTACATCT (SEQ ID NO: 4)
```

SYSTEMS AND METHODS FOR ANALYZING SEQUENCE DATA

SEQUENCE LISTING

This application contains a sequence listing which has been submitted in ASCII format via EFS-Web and is hereby incorporated by reference in its entirety. The ASCII-formatted sequence listing, created on Feb. 11, 2014, is named SBG-014-00US-sequences_ST25, and is 806 bytes in size.

FIELD OF THE INVENTION

The invention relates to analysis of genetic and genomic sequences.

BACKGROUND

Much information about a person's health is encoded in their DNA. Next-generation sequencing (NGS) technologies rapidly translate that information from its natural, biological format into files of sequence data that can be examined for disease-associated mutations and other features. However, as DNA sequencing technologies become faster, cheaper, and more accurate, the results produced by those sequencing technologies can become difficult to analyze.

It is now often the case that a researcher or medical professional will have to make sense of raw sequence data that is more complex than the linear sequence of "a gene" or even "a genome". Most genomic sequencing produces millions of reads that must be assembled together in order to make sense of the data. Due to heterozygosity, somatic mutations, repeated genetic elements, structural variants, sequencing errors, or other factors, sequence reads can be assembled in many ways, some of which have little, or even misleading, informatics content. Moreover, genomic sequencing is often more complex than simply sequencing an individual's genome. For example, researchers will study whole populations of related subjects, or will need to compare those results from one study with those results from another. Unfortunately, comparing one set of results with another often requires data-limiting simplifications. For example, reads are often assembled and then reduced to a consensus sequence for comparison to a reference, thus potentially ignoring sources of heterogeneity within those reads.

Some attempts have been made to represent genetic information using a data structure known as a directed acyclic graph (DAG). However, while a DAG can potentially represent known instances of heterogeneity, simply having a DAG does not address the problem of what to do with numerous complex sets of sequence data.

SUMMARY

The invention provides methods for comparing one set of genetic sequences to another without discarding any information within either set or otherwise sacrificing the breadth of information within either set of sequences for the sake of making the comparison. The invention includes methods of aligning two or more DAGs in order to produce an aligned DAG. The aligned DAG is simply the aligned combination of two or more DAGs and is similar to any of the original DAGs except that the input to the aligned DAG is always two or more DAGs as opposed to linear sequence. The aligned DAG can further be aligned to other DAGs or other aligned DAGs as described below.

Methods of the invention are useful to obtain a best-scoring DAG alignment based on weighted scores for matches, mis-matches, and gaps and can find the best scoring alignment even where each of the input sequence data sets to be aligned is structured to represent numerous different nucleotides or sequences at numerous different locations along a genome, that is, where each input sequence set is a structured as a non-linear representation of a plurality of aligned sequences such as a genomic sequence DAG.

Methods of the invention are useful to store sets of genetic sequences as a sequence DAG. A sequence DAG may be used to represent any multi-plex set of related nucleic acid or protein sequences such as, for example, a multiple sequence alignment of related genes, an assembly of NGS reads, or two or more reference genomes. Furthermore, methods of the invention may be used to align one sequence DAG to another, wherein the resulting alignment can be represented as a sequence DAG that can potentially represent a full multiple sequence alignment among all of the individual sequences that contributed to one of the paths through one of the initial sequence DAGs.

DAG-to-DAG alignment is a natural choice for many urgent applications. It is appropriate wherever a set of genomic information consisting of more than one string needs to be compared to any non-linear reference. For example, a subpopulation DAG could be compared to a population DAG in order to compare the genetic features of that subpopulation to those of the population. Similarly, a cancer DAG could be compared to a species, population, subpopulation, or familial DAG. In view of the fact that the progression of cancer may be viewed as rapid, numerous mutations in the genome, a DAG representing certain types of cancers may give a better understanding not only of the cause of cancer but of the cancer itself.

In certain aspects, the invention provides a method for genomic analysis. The method includes representing a plurality of nucleic acids as a reference directed acyclic graph (DAG), wherein a DAG comprises nodes, each node comprising a string of one or more nucleotides, and edges defining connections among the nodes, and further wherein one or more of the nodes each represent more than one of the plurality of nucleic acids. The method further includes obtaining a second DAG representing a second plurality of nucleic acids and finding an optimally-scoring alignment between the second DAG and the reference DAG. The second DAG can be obtained from any suitable source such as, for example, sequence reads from a sample from a subject. The reference DAG may represent a plurality of alleles associated with a disease.

Preferably the steps are performed using a computer system comprising a processor coupled to a non-transitory memory having the reference DAG stored therein and further wherein the optimally-scoring alignment is stored as a final DAG in the non-transitory memory. A DAG may be stored as a computer file in which each node comprises a character string and a label and each edge comprises a pair of labels.

Finding the best-scoring alignments between a reference DAG and a second DAG may be done by initializing a matrix or matrices with the nucleotides of the first DAG on one side or and those of the second DAG on the other side. As the figures indicate, representing this two-dimensionally can be difficult, because each DAG is itself more than one-dimensional and those DAGs do not map easily onto linear sides of matrices. However, the equations described herein describe straightforward recursive relationships between the matrix elements. The matrix cell with the highest value is identified after that recursive process is complete, and a path through the matrix is identified ending at that cell (e.g., using Smith-Waterman-type "backtracking" techniques). This path indicates the optimally-scoring or best-scoring alignment between the second DAG and the reference DAG.

In some embodiments, at least one path through the reference DAG represents a sequence of a human chromosome. At least one path through the second DAG may represent an alternative sequence of the human chromosome. Homozygous loci in the sample may be represented using a single node in the second DAG and heterozygous loci in the sample are represented using different nodes in the second DAG. In certain embodiments, the second DAG represents a transcriptome from an organism and the reference DAG represents one or more genomes from organisms of a same species as the organism. In some embodiments, the reference DAG comprises a plurality of binary alignment map (BAM) entries that have been mapped to a first genomic reference and the second DAG comprises a second plurality of BAM entries that have been mapped to a second genomic reference.

Aspects of the invention provide a method of identifying chromosomal structural variants. The method includes obtaining a plurality of paired-end reads from a nucleic acid sample, each comprising an upstream pair member and a downstream pair member and characterized by an insert length approximating a number of nucleotides spanning a distance from an upstream end of the upstream pair member to a downstream end of the downstream pair member. The upstream pair member of each of the plurality of paired-end reads is mapped to a reference. A subset of the plurality of paired-end reads for which the upstream pair members map to the reference within a pre-defined cluster is found. For the subset of the plurality of paired-end reads, the downstream pair members are assembled into a DAG that represents one or more chromosomal structural variants within the sample.

In other aspects, the invention provides a method of identifying haplotypes. The method includes obtaining a plurality of sequence reads from a number k of diploid genomes, assembling the reads into a DAG representing optimally-scoring alignments among the sequence reads, and determining support for each of a plurality of paths through the DAG according to a number of reads consistent with a location in that path that is consistent with fewer reads than any other location in that path. A number of the paths meeting some pre-determined support criteria are identified as describing relevant haplotypes. In some embodiments, the pre-determined support criteria includes identifying a number n of paths for which the support meets a constraint and identifying the min(n, k) best-supported of the paths as the relevant haplotypes.

BRIEF DESCRIPTION OF THE DRAWINGS

FIG. 2 shows the actual matrices that correspond to the comparison.

DETAILED DESCRIPTION

Figure 1:
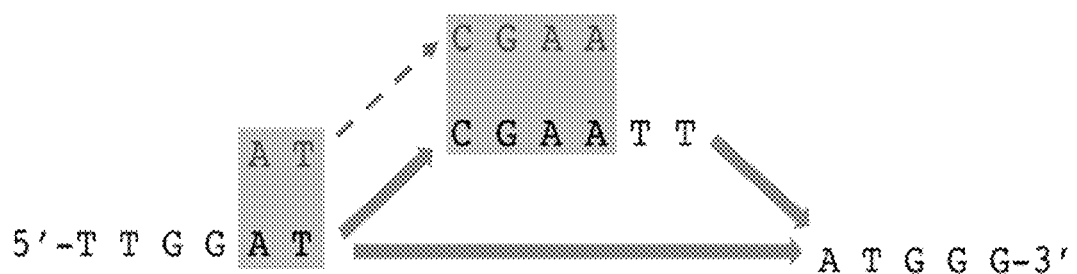
FIG. 1 represents a read being compared to a DAG.

Embodiments of the invention provide for the alignment of one sequence DAG to another sequence DAG. A DAG is a mathematical data structure that may be represented as a graph, but that is not necessarily ever instantiated as a visible graph. A DAG is a data structure that has nodes connected by directed edges, wherein no single path through the DAG traverses the same node more than once and thus does not include any cycles. "DAG" can refer to a graph, the underlying data structure, or both, and as used herein, "sequence DAG" refers to a DAG representing biological sequences. A sequence DAG may be a record stored in a non-transitory, computer-readable medium that includes nodes connected by edges, in which each node includes a string of one or more nucleotide characters with a 5'-3' directionality and each edge extends from a 3' end of the character string of one node to a 5' end of a string of another node. At least one node will be a source in that it has no edges connected to the 5' end of its character string. At least one node will be a sink in that it has no edges connected to the 3' end of its character string. What characters are permitted may depend on the embodiment or implementation, and in some embodiments, the permitted characters include the IUPAC nucleotide codes (either A, T, C, and G, with or without U or N, or the complete set of IUPAC ambiguity codes).

1. Alignments

The invention provides methods for aligning one or more sequence DAGs to one another. Alignment generally involves placing one sequence along another sequence, gaps may be introduced along each sequence, scoring how well the two sequences match, and preferably repeating for various position along one or more of the sequences. The best-scoring match is deemed to be the alignment and represents an inference about the historical relationship between the sequences. Some analysis projects may seek an optimal scoring alignment that is not also a highest scoring alignment, and methods of the invention may be used to find the optimally scoring alignment. For example, where gene duplication has created copies of a gene that descend side by side during the history of an organism, (e.g., alpha and beta hemoglobin) the genes may be called paralogous genes. Fitch, 1970, Distinguishing homologous from analogous proteins, Systematic Zoology 19:99-113. A researcher studying two paralogous genes in an organism's genome may obtain sequence reads from one of those genes. The researcher may wish to compare a sequence read DAG from the one gene to a genomic DAG that represents a plurality of known genomes for that organism. In some instances, the read DAG may have a higher-scoring alignment to the second, paralogous gene (e.g., due to mutations in the researcher's sample) than to the one gene. In that sense, the researcher has a priori information that the alignment of the read DAG to the one gene in the genomic DAG is the optimal alignment, even though it is not the highest-scoring or best-scoring alignment. Methods of the invention may be used to find that optimal alignment by excluding the other alignment results from consideration. Thus the invention provides methods that may be used to find an alignment between two or more sequence DAG. In some embodiments, the resulting aligned DAG will represent an optimal alignment. That optimal alignment may be a best-scoring DAG matrix alignment produced by a combination of the two sequence-DAGs. The best-scoring DAG alignment may be determined by the mathematical construct as described herein, representing the optimal path through a matrix of similarity scores.

In a pairwise alignment, a base in one sequence alongside a non-matching base in another indicates that a substitution mutation has occurred at that point. Similarly, where one sequence includes a gap alongside a base in the other sequence, an insertion or deletion mutation (an "indel") may be inferred to have occurred.

In some embodiments, scoring an alignment of a pair of nucleic acid sequences involves setting values for the probabilities of substitutions and indels. When individual bases are aligned, a match or mismatch contributes to the alignment score by a score or a penalty, which could be, for example, a match score of 1 for a match and a mismatch penalty of −0.33 for a mismatch. An indel deducts from an alignment score by a gap penalty, which could be, for example, −1. Scores and penalties can be based on empirical knowledge or a priori assumptions about how sequences evolve. Their values affects the resulting alignment. Particularly, the relationships among score and penalty values influence whether substitutions or indels will be favored in the resulting alignment. Additional helpful discussion may be found in Rodelsperger, 2008, Syntenator: Multiple gene order alignments with a gene-specific scoring function, Alg Mol Biol 3:14; Yanovsky, et al., 2008, Read mapping algorithms for single molecule sequencing data, Procs of the 8th Int Workshop on Algorithms in Bioinformatics 5251: 38-49; Hein, 1989, A new method that simultaneously aligns and reconstructs ancestral sequences for any number of homologous sequences, when phylogeny is given, Mol Biol Evol 6(6):649-668; Schwikowski & Vingron, 2002, Weighted sequence graphs: boosting iterated dynamic programming using locally suboptimal solutions, Disc Appl Mat 127:95-117, the contents of each of which are incorporated by reference.

Stated formally, a pairwise alignment represents an inferred relationship between two sequences, x and y. For example, in some embodiments, a pairwise alignment A of sequences x and y maps x and y respectively to another two strings x' and y' that may contain spaces such that: (i) |x'|=|y'|; (ii) removing spaces from x' and y' should get back x and y, respectively; and (iii) for any i, x'[i] and y'[i] cannot be both spaces.

A gap is a maximal substring of contiguous spaces in either x' or y'. Pairwise alignment A can include the following three kinds of regions: (i) matched pair (e.g., x'[i]=y'[i]; (ii) mismatched pair, (e.g., x'[i]≠y'[i] and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

In some embodiments, any pair has a score a defined by a 4×4 matrix B of scores/penalties. For example, B[i,i]=1 and 0<B(i,j)i<>j<1 is one possible scoring system. For instance, where a transition is thought to be more biologically probable than a transversion, matrix B could include B[C,T]=0.7 and B[A,T]=0.3, or any other set of values desired or determined by methods known in the art.

Alignment according to some embodiments of the invention generally involves—for sequence Q (query) having m characters and a reference genome T (target) of n characters—finding and evaluating possible local alignments between Q and T. For any 1≤i≤n and 1≤j≤m, the largest possible alignment score of T[h . . . i] and Q[k . . . j], where h≤i and k≤j, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48(3):443-453, 1970) and Smith-Waterman (J Mol Biol, 147(1):195-197, 1981; Adv. in Math. 20(3), 367-387, 1976). A further improvement to Smith-Waterman by Gotoh (J Mol Biol, 162(3), 705-708, 1982) reduces the calculation time from O(m2n) to O(mn) where m and n are the sequence sizes being compared and is more amendable to parallel processing. In the field of bioinformatics, it is Gotoh's modified algorithm that is often referred to as the Smith-Waterman algorithm.

Smith-Waterman-type algorithms align linear sequences by rewarding overlap between bases in the sequences, and penalizing gaps between the sequences. Smith-Waterman also differs from Needleman-Wunsch, in that Smith-Waterman does not require the shorter sequence to span the string of letters describing the longer sequence. That is, Smith-Waterman does not assume that one sequence is a read of the entirety of the other sequence. Furthermore, because Smith-Waterman is not obligated to find an alignment that stretches across the entire length of the strings, a local alignment can begin and end anywhere within the two sequences. Smith-Waterman algorithms, and implementations thereof, are described in more detail in U.S. Pat. No. 5,701,256 and U.S. Pub. 2009/0119313, both herein incorporated by reference in their entirety.

Smith-Waterman type algorithms may be used to perform a pairwise alignment of two sequences a and b of length n and m by first calculating values for entries h[i,j] in an n×m matrix H of similarity (or distance) scores and then finding a trace through that matrix according to the steps described below. First, the matrix is initialized by assigning h[i,0]=h[0,j]=0, for 0≤i≤n and 0≤j≤m. Note that i and j are indices of a and b so that a[i] is the ith nucleotide in a.

Then, for each remaining entry h[i,j], the neighbors to the left, above, and to the above-left of that entry are evaluated to find the highest scoring one of those entries. In a two dimensional matrix (e.g., during pairwise alignment), those three cells to the left, above, and diagonally to the left and above h[i,j] would be h[i−1,j], h[i,j−1], and h[i−1,j−1].

An association is recorded between that entry h[i,j] and the highest valued of h[i−1,j], h[i,j−1], and h[i−1,j−1]. A value is calculated for h[i,j] based on the value of that associated entry. The association can be thought of as a pointer from entry h[i,j] to its highest-valued neighbor, and this pointer will be "looked at" later, when it used to find a trace through the matrix. The value assigned to h[i,j] is:

$$\max\{h[i-1,j-1]+s(a[i],b[j]),h[i-1,j]-W,h[i,j-1]-W,0\}$$

In the equations above, s(a[i],b[j]) represents either a match bonus (when a[i]=b[j]) or a mismatch penalty (when a[i]≠b[j]), and W represents a penalty for gap in either a or b. Gap penalty W may preferably include an opening component and an extension component, discussed later.

Once values have been assigned for every entry h[i,j] in H, a trace is found through the matrix by the following steps. First, the highest-valued entry h[i,j] is identified. Then—remembering that each entry is associated with one upstream neighbor—entries in H are traced sequentially from the highest-valued entry following the associations, or "pointers", until a zero entry is reached. The resulting trace will originate at the highest-valued entry and extend "back" (i.e., towards h[0,0]) to its terminus at the first zero entry encountered by following the pointers. That trace (sometimes called a traceback in the literature) indicates the optimally-scoring alignment between the sequences a and b. That is, the optimally-scoring alignment can be read by writing out the indices of each entry in the trace in their order within the trace and supplying a "-" character where the trace extends off-diagonal, and then using the indices as indices of a and b to retrieve the corresponding nucleotide characters from a and b. Thus if a trace extends through h[3,3], h[4,4], h[4,5], h[4,6], h[5,7], the paired indices will be:

3 4 - - 5
3 4 5 6 7

Smith-Waterman type alignment may be employed using dynamic programming. This dynamic programming technique employs tables or matrices to preserve match scores and avoid re-computation for successive cells.

To formalize the foregoing description for programming, and to give an example set of values for the bonuses and penalties, the following steps are given. Note that in the above, a single gap penalty was used. In the below, separate insertion and deletion penalties are tracked. Either approach may be used and one of skill in the art may choose one over the other for extrinsic reasons such as a priori knowledge of likelihoods of certain sequence evolution events.

Each element of a string is indexed with respect to a letter of the sequence, that is, if S is the string ATCGAA, S[1]=A.

For a matrix B, entries B[j,k] are given in equation (2) below:

$$B[j,k]=\max(p[j,k],i[j,k],d[j,k],0) \text{ (for } 0 \le j \le m, 0 \le k \le n) \quad (2)$$

The arguments of the maximum function, B[j,k], are outlined in equations (3)-(5) below, wherein MISMATCH_PENALTY, MATCH_BONUS, INSERTION_PENALTY, DELETION_PENALTY, and OPENING_PENALTY are all constants, and all negative except for MATCH_BONUS. The match argument, p[j,k], is given by equation (3), below:

$$p[j,k]=\max(p[j-1,k-1],i[j-1,k-1],d[j-1,k-1])+\text{MISMATCH\_PENALTY, if } S[j] \ne A[k] \quad (3)$$

$$=\max(p[j-1,k-1],i[j-1,k-1],d[j-1,k-1])+\text{MATCH\_BONUS, if } S[j]=A[k]$$

the insertion argument i[j,k], is given by equation (4), below:

$$i[j,k]=\max(p[j-1,k]+\text{OPENING\_PENALTY},i[j-1,k],d[j-1,k]+\text{OPENING\_PENALTY})+\text{INSERTION\_PENALTY} \quad (4)$$

and the deletion argument d[j,k], is given by equation (5), below:

$$d[j,k]=\max(p[j,k-1]+\text{OPENING\_PENALTY},i[j,k-1]+\text{OPENING\_PENALTY},d[j,k-1])+\text{DELETION\_PENALTY} \quad (5)$$

For all three arguments, the [0,0] element is set to zero to assure that the backtrack goes to completion, i.e., p[0,0]=i[0,0]=d[0,0]=0.

The scoring parameters may be adjusted according to the project. One example of the scoring parameter settings (Huang, Chapter 3: Bio-Sequence Comparison and Alignment, ser. Curr Top Comp Mol Biol. Cambridge, Mass.: The MIT Press, 2002) for DNA would be:

MATCH_BONUS: 10
MISMATCH_PENALTY: −20
INSERTION_PENALTY: −40
OPENING_PENALTY: −10
DELETION_PENALTY: −5

The relationship between the gap penalties (INSERTION_PENALTY, OPENING_PENALTY) above help limit the number of gap openings, i.e., favor grouping gaps together, by setting the gap insertion penalty higher than the gap opening cost. Of course, alternative relationships between MISMATCH_PENALTY, MATCH_BONUS, INSERTION_PENALTY, OPENING_PENALTY and DELETION_PENALTY are possible.

2. Sequence DAG Alignments

The foregoing describes a formalism of a Smith-Waterman type alignment that is conducive to implementation by dynamic programming. One benefit of the invention includes the insight that the alignment algorithm, thus formalized, may be extended to a non-linear sequence structure such as a sequence DAG. Such an extended implementation may be referred to as a multi-dimensional Smith-Waterman type alignment. Such multi-dimensional algorithms of the invention provide for a "look-back" through a multi-dimensional space that includes multiple pathways and multiple nodes. The multi-dimensional algorithm identifies the maximum score at each position on the DAG (e.g., the reference sequence construct). In fact, by looking "backwards" at the preceding positions, it is possible to identify the optimum alignment across a plurality of possible paths.

A sequence DAG may be stored as a list of nodes and edges. One way to do this is to create a text file that includes all nodes, with an ID assigned to each node, and all edges, each with the node ID of starting and ending node. Thus, for example, were a DAG to be created for two sentences, "See Jane run," and "Run, Jane run,", a case-insensitive text file could be created. Any suitable format could be used. For example, the text file could include comma-separated values. Naming this DAG "Jane" for future reference, in this format, the DAG "Jane" may read as follows: 1 see, 2 run, 3 jane, 4 run, 1-3, 2-3, 3-4. One of skill in the art will appreciate that this structure is easily applicable to the sequences represented in FIGS. 1 and 7, for example, and the accompanying discussion below.

In certain embodiments, a DAG is stored as a table representing a matrix (or an array of arrays or similar variable structure representing a matrix) in which the (i,j) entry in the matrix denotes whether node i and node j are connected. For the DAG to be acyclic simply requires that all non-zero entries be above the diagonal (assuming indices are correctly ordered). In a binary case, a 0 entry represents that no edge is exists from node i to node j, and a 1 entry represents an edge from i to j. One of skill in the art will appreciate that a matrix structure allows values other than 0 to 1 to be associated with an edge. For example, any entry may be a numerical value indicating a weight, or a number of times used, reflecting some natural quality of observed data in the world. A matrix can be written to a text file as a table or a linear series of rows (e.g., row 1 first, followed by a separator, etc.), thus providing a simple serialization structure.

One useful way to serialize a matrix DAG would be to use comma-separated values for the entries, after defining the nodes. Using this format, the DAG "Jane" would include the same node definitions as for above, followed by matrix entries. This format could read as:

1 see, 2 run, 3 jane, 4 run
,,1,\,,1,\,,,1\,,, where zero (0) entries are simply omitted and '\' is a newline character.

Embodiments of the invention include storing a sequence DAG in a language built with syntax for graphs. For example, The DOT Language provided with the graph visualization software package known as Graphviz provides a data structure that can be used to store a DAG with auxiliary information and that can be converted into graphic file formats using a number of tools available from the Graphviz web site. Graphviz is open source graph visualization software. Graph visualization is a way of representing structural information as diagrams of abstract graphs and networks. It has important applications in networking, bioinformatics, software engineering, database and web design, machine learning, and in visual interfaces for other technical domains. The Graphviz programs take descriptions of graphs in a simple text language, and make diagrams in useful formats, such as images and SVG for web pages; PDF or Postscript for inclusion in other documents; or display in an interactive graph browser.

In an intermediate extension of Smith-Waterman type alignments, a sequence string is aligned to a sequence DAG, and a discussion of this will aid in understanding and implementing a full DAG-to-DAG alignment.

For aligning a string to a DAG, let S be the string being aligned, and let D be the directed acyclic graph to which S is being aligned. The elements of the string, S, are bracketed with indices beginning at 1. Thus, if S is the string ATC-GAA, S[1]=A, S[4]=G, etc.

In certain embodiments, for the DAG, each letter of the sequence of a node will be represented as a separate element, d. A predecessor of d is defined as:

(i) If d is not the first letter of the sequence of its node, the letter preceding d in its node is its (only) predecessor;

(ii) If d is the first letter of the sequence of its node, the last letter of the sequence of any node (e.g., all exons upstream in the genome) that is a parent of d's node is a predecessor of d.

The set of all predecessors is, in turn, represented as P[d].

In order to find the "best" alignment, the algorithm seeks the value of M[j,d], the score of the optimal alignment of the first j elements of S with the portion of the DAG preceding (and including) d. This step is similar to finding Hi,j in equation 1 above. Specifically, determining M[j,d] involves finding the maximum of a, i, e, and 0, as defined below:

$$M[j,d] = \max\{a, i, e, 0\} \quad (6)$$

where
e=max{M[j, p*]+DELETE_PENALTY} for p* in P[d]
i=M[j−1, d]+INSERT_PENALTY
a=max{M[j−1, p*]+MATCH_SCORE} for p* in P[d], if S[j]=d;
max{M[j−1, p*]+MISMATCH_PENALTY} for p* in P[d], if S[j]≠d As described above, e is the highest of the alignments of the first j characters of S with the portions of the DAG up to, but not including, d, plus an additional DELETE_PENALTY. Accordingly, if d is not the first letter of the sequence of the node, then there is only one predecessor, p, and the alignment score of the first j characters of S with the DAG (up-to-and-including p) is equivalent to M[j,p]+DELETE_PENALTY. In the instance where d is the first letter of the sequence of its node, there can be multiple possible predecessors, and because the DELETE_PENALTY is constant, maximizing [M[j, p*]+DELETE_PENALTY] is the same as choosing the predecessor with the highest alignment score with the first j characters of S.

In equation (6), i is the alignment of the first j−1 characters of the string S with the DAG up-to-and-including d, plus an INSERT_PENALTY, which is similar to the definition of the insertion argument in the pairwise case.

Additionally, a is the highest of the alignments of the first j characters of S with the portions of the DAG up to, but not including d, plus either a MATCH_SCORE (if the jth character of S is the same as the character d) or a MISMATCH_PENALTY (if the jth character of S is not the same as the character d). As with e, this means that if d is not the first letter of the sequence of its node, then there is only one predecessor, i.e., p. That means a is the alignment score of the first j−1 characters of S with the DAG (up-to-and-including p), i.e., M[j−1,p], with either a MISMATCH_PENALTY or MATCH_SCORE added, depending upon whether d and the jth character of S match. In the instance where d is the first letter of the sequence of its node, there can be multiple possible predecessors. In this case, maximizing {M[j, p*]+MISMATCH_PENALTY or MATCH_SCORE} is the same as choosing the predecessor with the highest alignment score with the first j−1 characters of S (i.e., the highest of the candidate M[j−1,p*] arguments) and adding either a MISMATCH_PENALTY or a MATCH_SCORE depending on whether d and the jth character of S match.

Again, as in the SW algorithm, the penalties, e.g., DELETE_PENALTY, INSERT_PENALTY, MATCH_SCORE and MISMATCH_PENALTY, can be adjusted to encourage alignment with fewer gaps, etc.

As described in the equations above, the algorithm finds the optimal alignment for a sequence to a DAG by calculating not only the insertion, deletion, and match scores for that element, but looking backward (against the direction of the DAG) to any prior nodes on the DAG to find a maximum score. Thus, the algorithm is able to traverse the different paths through the DAG. The backtraces follow the best alignment and extend toward the origin of the graph, and identify the most likely alignment within a high degree of certainty.

Implementation of the disclosed algorithm is exemplified in FIG. 1, where a sequence "ATCGAA" is aligned against a DAG that represents a reference sequence TTGGATATGGG (SEQ ID NO: 1) and a known insertion event TTGGAT<u>CGAATT</u>ATGGG (SEQ ID NO: 2), where the insertion is underlined.

FIG. 1 shows a pictorial representation of the read ("ATCGAA") being compared to the DAG. The top area of FIG. 1 presents a reference sequence TTGGATATGGG (SEQ ID NO: 1) and a known insertion event TTGGAT<u>CGAATT</u>ATGGG (SEQ ID NO: 2) (here, the insertion is underlined). The bottom area of FIG. 1 shows the alignment constructed using a DAG. In the depicted DAG, SEQ ID NOS. 1 and 2 can both be read by reading from the 5' end of the DAG to the 3' end of the DAG, albeit along different paths. The sequence read is shown as aligning to the upper path as depicted.

Figure 2:
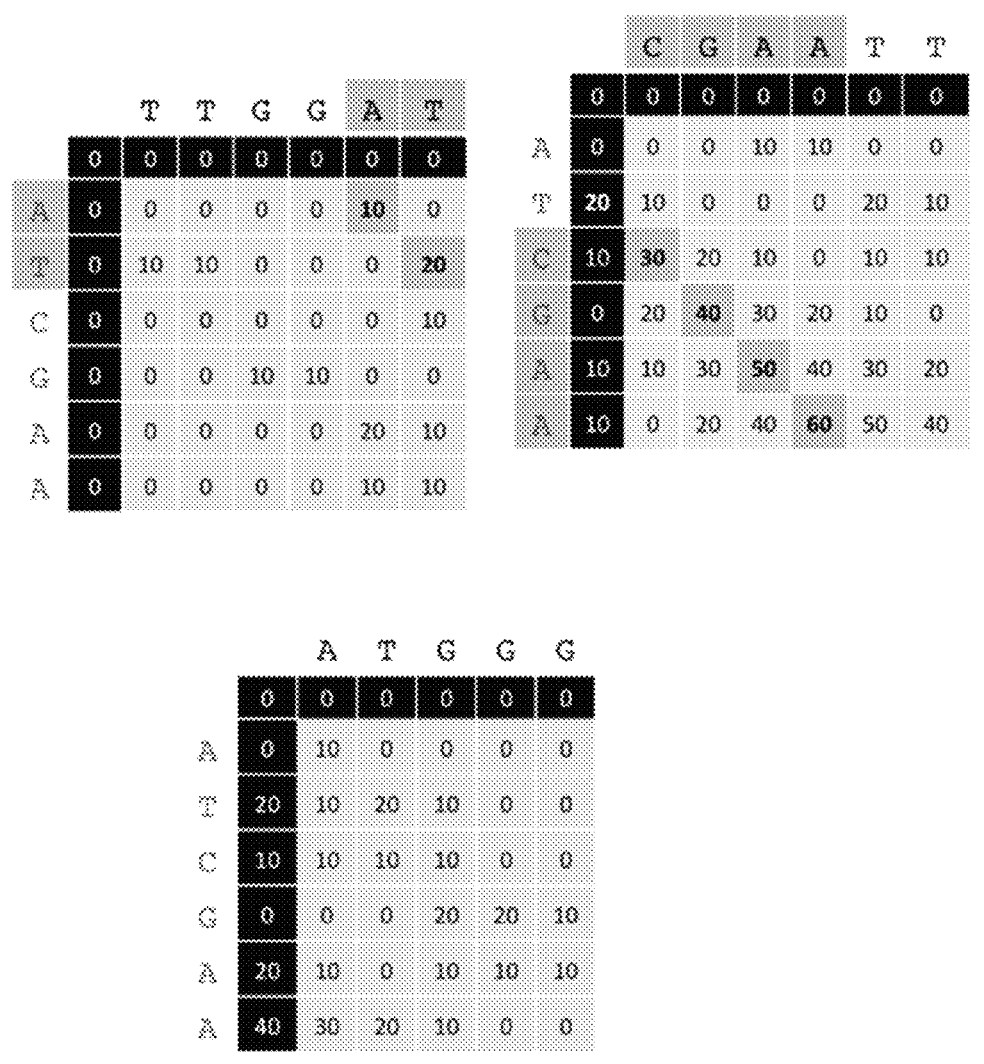

FIG. 2 shows the actual matrices that correspond to the comparison. Like the Smith-Waterman technique, the illustrated algorithm of the invention identifies the highest score and performs a backtrack to identify the proper location of the read. FIGS. 1 and 2 also highlight that the invention produces an actual match for the string against the construct.

In the instances where the sequence reads include variants that were not included in the DAG, the aligned sequence will be reported out with a gap, insertion, etc.

One sequence DAG can be aligned to another sequence DAG to generate an aligned DAG by generalizing the foregoing in a method that includes first calculating values for entries in an array of pairwise match scores between characters from the respective sequence DAGs and then tracing along series of adjacent, associated elements in that array to find best-scoring alignments between paths through the respective DAGs. All of those resulting best-scoring alignments can be presented or stored as an aligned DAG. The aligned DAG is the aligned combination of the two sequence DAGs and is structurally similar to any of the original DAGs except that the input to the aligned DAG is always two or more DAGs as opposed to linear sequence. The aligned DAG can further be aligned to other DAGs or other aligned DAGs as described below The algorithmic modifications one must apply to the string-to-DAG algorithm in order to get a DAG-to-DAG algorithm are analogous to those applied to the string-to-string algorithm in order to get a string-to-DAG algorithm. In that case, we replaced terms such as i−1, where i represents an index, with P[i], where P[i] represents all immediate predecessors of the node with index i. One way to think about the modification is that finding the character with location i−1 in a string is a special case of picking out the set of predecessors: in a (linear) string, there is only one predecessor to the location with index i, and that is the location with index i−1, so insofar as a dynamic programming algorithm requires the consideration of some value for all predecessors of a location with index i, we can simply examine that value for the location with index i−1.

Considering the string-to-DAG equations as they appear above, we notice that various "j−1" terms, where j represents the index of a location in a string, still appear. Just as we moved from i−1 to P[i] in order to get the full set of predecessors in a DAG, we need to move from j−1 to P[j] to get the full set of predecessors of the object that is being aligned to the DAG, since this is no longer a string but itself a DAG. Thus, for example, we replace the e-term that is currently:

e=max{M[j,p*]+DELETE_PENALTY} for p* in P[d]
with:
e=max{M[p*, p**]+DELETE_PENALTY} for p* in P[d] and p** in P[d']

Other terms are to be modified analogously, so that we have:

M[j,d]=max{a,i,e,0}
where
e=max{M[p*, p**]+DELETE_PENALTY} for p* in P[j] and p** in P[d]
i=max{M[p*, d]+INSERT_PENALTY} for p* in P[j]
a=max{M[p*, p**]+MATCH_SCORE} for p* in P[j] & p** in P[d], if S[j]=d;
   max{M[p*, p**]+MISMATCH_PENALTY} for p* in P[j] and p** in P[d], if S[j]≠d Although it is common to consider alignments of one string to another, and although we have shown how to generalize this process by replacing strings with DAGs, most people think of a process or result, not an object, when they speak of "alignments." We observe, however, that the output of an alignment process, because it contains information about the relationship of one genetic item to another, can be represented not only as a located string or a compact idiosyncratic gapped alignment report (CIGAR) string, e.g., a CIGAR string in a BAM format file, but also as a DAG.

For discussion of file formats, see Li, et al., 2009, The Sequence Alignment/Map format and SAMtools, Bioinformatics 25(16):2078-9 and Li et al., 2009, SOAP2: an improved ultrafast tool for short read alignment, Bioinformatics 25(15):1966-7, both incorporated by reference.

Because DAG-to-DAG alignment is possible, and because alignments can be viewed as DAGs, it is possible to align alignments to alignments. A set of BAM entries, for example, can be converted to DAGs and aligned to each other. Indeed, BAMs that have been generated relative to different references can be aligned against each other. Given the quantity of existing BAM files and the variety of references to which those files correspond, the ability to directly compare entries from BAMs with different references would be valuable, and these techniques remove barriers to our gaining that ability.

One can convert a BAM entry to a DAG by using the relevant reference and the CIGAR string for the given entry, because BAM sequence entries, CIGAR strings, and references—taken together—contain enough information to construct a DAG representing the alignment. With reference to Table 1 of Li, et al., 2009, The Sequence Alignment/Map format and SAMtools, Bioinformatics 25(16):2078-9, we see that the fourth mandatory field in the SAM format is POS, 1-Based leftmost POSition of clipped alignment.

Suppose that in a given BAM entry, we have in the SEQ field:

(SEQ ID NO: 3)
GATTACACATGATTACATGACTGACCATTCCAT

The POS field tells us to look at position 1,525,334 in the reference, where we find:

(SEQ ID NO: 4)
GAGTACAGATTACATGACTGACGGAGCATTACATCT . . .

In the CIGAR field, we find:
M7I3M15D4M8

We begin by examining the first seven characters of each sequence, because those correspond to portions that aligned to each other. Note that this does not entail that there are no mismatches:

GATTACA

GAGTACA

We see that there is a mismatch in position 3.

Figure 3:
FIG. 3 illustrates a DAG that obtains from a first step in building a sequence DAG.
Figure 3:
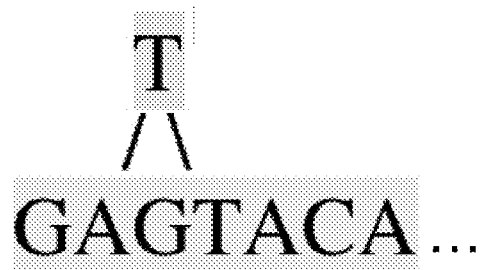
Figure 4:
FIG. 4 shows how an initial DAG is built up by alignment.
Figure 4:
Figure 5:
FIG. 5 shows a DAG continuing to grow.
Figure 5:
Figure 6:
FIG. 6 illustrates a sequence DAG that is nearly complete.
Figure 6:
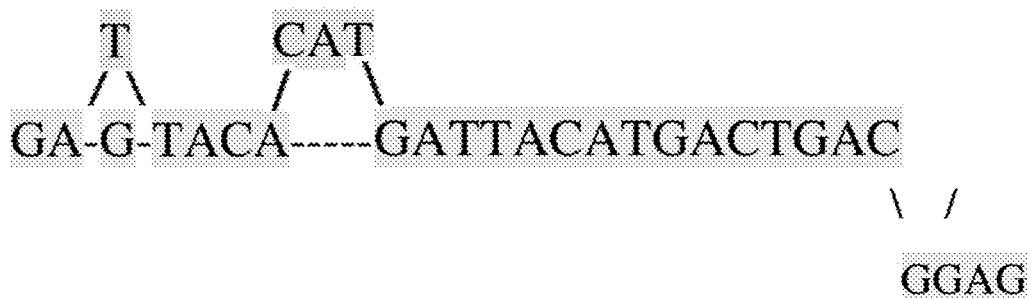
Figure 7:
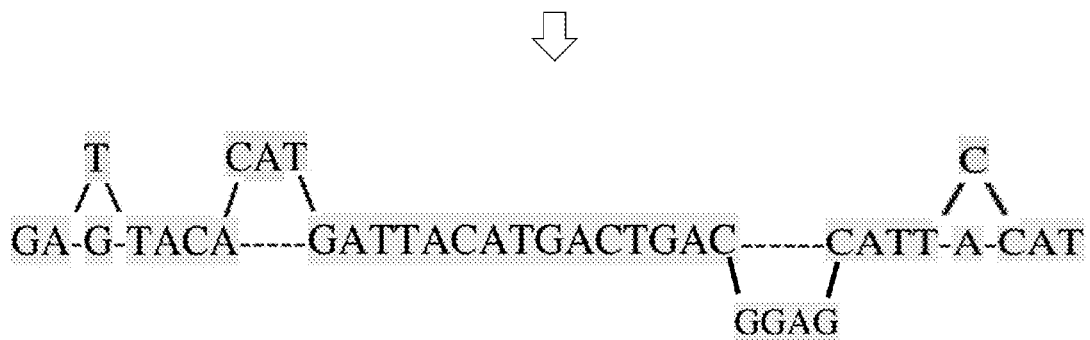
FIG. 7 depicts the complete DAG
FIG. 8 diagrams a method of DAG-to-DAG alignment

FIG. 3 illustrates the DAG that is produced from a first step in building a sequence DAG. The "I3" portion of the CIGAR string indicates an insertion of three bases, so we can continue. FIG. 4 shows the DAG that represents a DAG as it grows. The "M15" indicates that the next fifteen characters of each string are aligned as a group. These indeed match, so we continue. FIG. 5 illustrates the DAG resulting from this step. The "D4" indicates that the next four bases from the reference are deleted, leading to the DAG shown in FIG. 6. FIG. 6 illustrates a sequence DAG as it is being built. Finally, the last eight bases are treated as an aligned unit, and we find one mismatch. This produces our final DAG, shown in FIG. 7. FIG. 7 depicts the complete DAG representing the alignment described by the hypothetical BAM entry.

That completed DAG as depicted in FIG. 7 is an example of a sequence DAG. The sequence DAG is created in a way that reflects the scoring given by a Smith-Waterman-type alignment algorithm and the sequence DAG can further be aligned to another sequence DAG.

Figure 8:
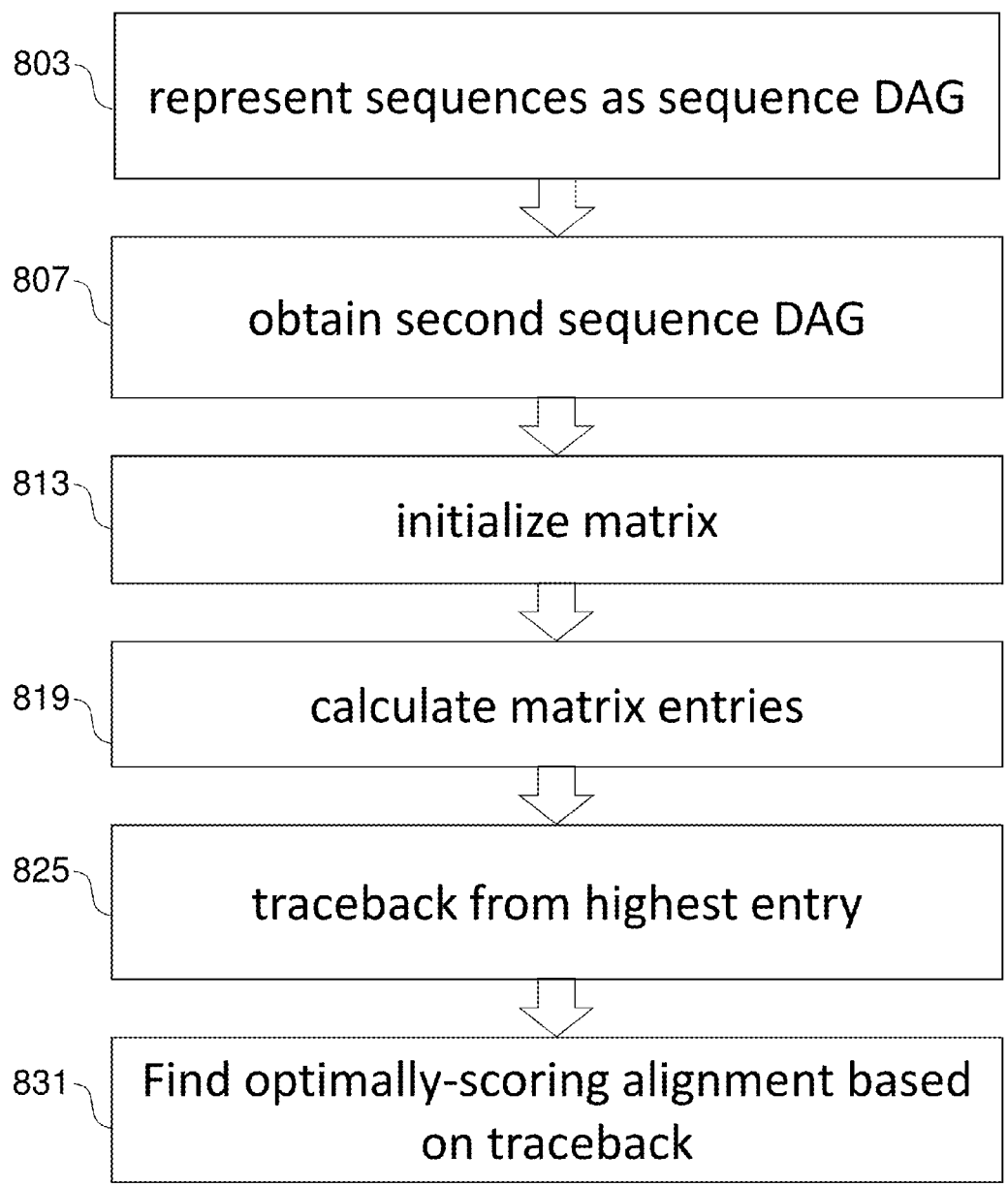

FIG. 8 diagrams a method of DAG-to-DAG alignment according to embodiments of the invention. In general, the method includes the following steps.

Represent 803 a plurality of nucleic acids as a reference directed acyclic graph (DAG), wherein a DAG comprises nodes, each node comprising a string of one or more nucleotides, and edges defining connections among the nodes, and further wherein one or more of the nodes each represent more than one of the plurality of nucleic acids.

Obtain 807 a second DAG representing a second plurality of nucleic acids.

Initialize 813 a matrix of similarities between nucleotides in the reference DAG and nucleotides in the second DAG by setting all edge entries to be zero, wherein an edge entry is an entry with no more than 1 non-zero index.

For each non-edge entry, associate that entry with a highest-value upstream neighbor entry of that entry and calculate 819 a value for that entry with a value based on the highest-value upstream neighbor entry, wherein an upstream neighbor entry has indices that each differ by −1 or 0, at least one index differing by −1, from the corresponding indices of that entry being populated.

Identify 831 a traceback path through the matrix that originates at the entry with the highest value and traces sequentially through each associated highest-value upstream neighbor until a zero entry is met at which zero entry the path terminates, wherein the identified path indicates the optimally-scoring alignment between the second DAG and the reference DAG.

Find an optimally-scoring alignment between the second DAG and the reference DAG. The alignment of one sequence DAG to another, as described, proceeds through the use of a matrix of similarities (or distances) and produces an aligned DAG. In that sense, the aligned DAG may be referred to as a "DAG matrix alignment" and so may the procedure of aligning sequences, sequence DAGs, or a combination thereof through the use of a similarity matrix to produce a DAG of aligned sequences may be referred to as performing a DAG matrix alignment.

One feature of the invention that is helpful to recognize is that methods of the invention may be used to find an alignment between two or more sequence DAGs and, depending on the nature or objectives of the work being done, the obtained alignment may be, but need not be, the "highest scoring" alignment nor even an optimally-scoring alignment. For example, some researchers may calculate both a similarity and a distance score by supplying different match and mismatch penalties. Since distance is a measure of a number of differences, and similarity is a measure of (roughly) a number of matches, the sign of the score would change depending on which is calculated. Further, where the two sequences TGC and TCC have certain a similarity score and a certain distance score, the two sequences TAACTAGC and TAACTACC would have the same distance score but a much higher similarity score.

3. Local Heuristic Assembly

A related but distinct innovation is "local heuristic assembly." This process could be used to solve a persistent problem in the analysis of short reads: that of inferring the sequences of repetitive regions, tandem duplications, indels, and other structural variants.

There are two major obstacles to such inference. First, structural variants are so large that reads are simply thrown away as unalignable rather than recognized as arising from a certain region. Second, repetitive regions will align so well to many locations that it can be difficult to know which of those many locations corresponds to the real origin of the read. These obstacles are somewhat independent; each can occur without the other. Many structural variants are, however, repetitive regions, and many repetitive regions are likely candidates for being inserted or deleted in one sample relative to another (which is why they are repetitive in the first place).

The invention provides systems and methods for inferring the sequences of repetitive regions, tandem duplications, indels, and other structural variants based on paired-end data. Methods of the invention include aligning a plurality of paired-end reads to the reference, identifying a set of unaligned reads from the plurality of paired-end reads that did not align to the reference according to some criterion, and—for the set of unaligned reads—finding clusters of those unaligned paired-end reads for which a portion of reads map to the same part of the genome.

Any suitable method may be used find the clusters. Once one has mapped the beginnings of (paired-end) reads as far as they can be mapped, and associated those beginnings-of-reads with genomic locations, any known clustering method could in theory be used to sort those into clusters. In practice, it will likely be more reasonable simply to search for windows of R base pairs in which sufficiently many reads map. (We might take R to be equal to read length of a given set of short reads.) Clusters, in cases both of split reads and read-pairs, are discussed and illustrated in Stewart, et al., 2011, A comprehensive map of mobile element insertion polymorphisms in humans, PLoS Genetics 7(8):1-19, incorporated by reference.

Figure 9:
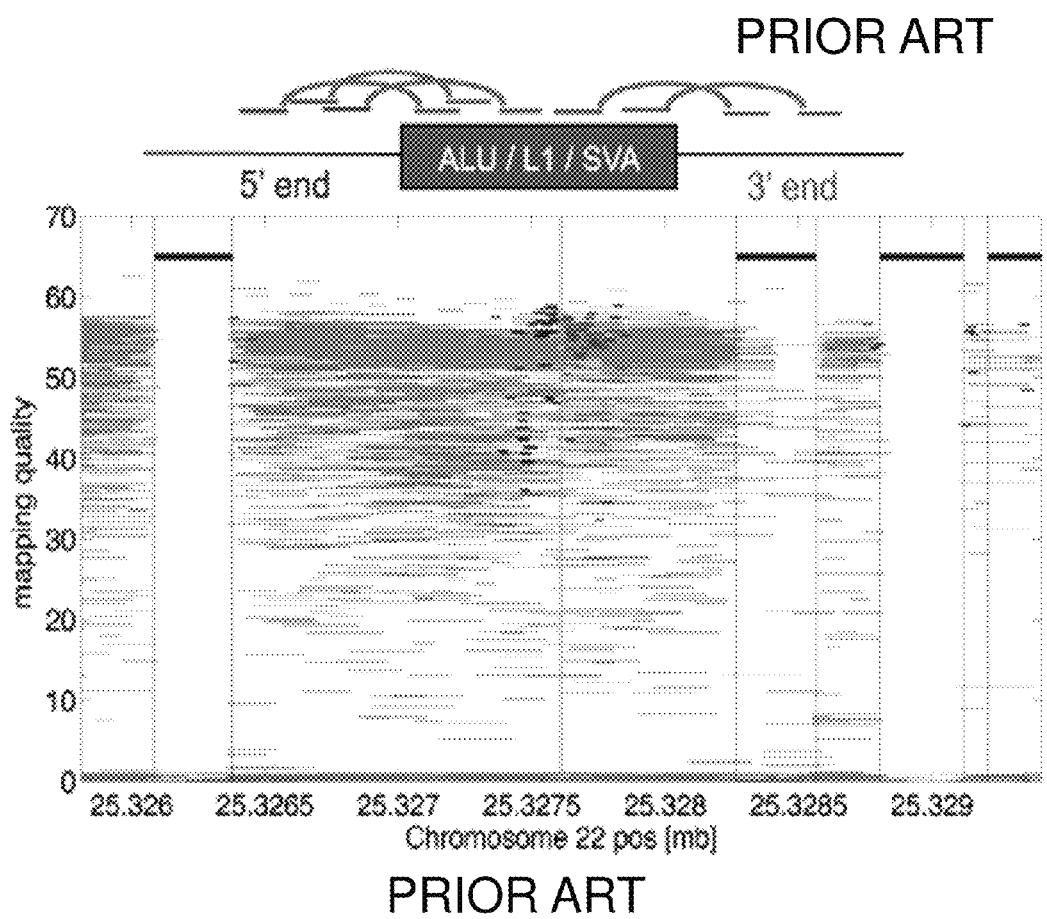
FIG. 9 shows a prior art approach to detecting structural variants.

FIG. 9, reproduced from FIG. 1 in Stewart, et al., 2011, A comprehensive map of mobile element insertion polymorphisms in humans, PLoS Genetics 7(8):1-19, illustrates a prior art method for the detection of non-reference mobile element inserts (MEI). That method can use a read-pair constraint (RP) method applied to Illumina paired-end short read data and a split-read (SR) method applied to the longer read data from Roche/454 pyrosequencing. FIG. 9 shows the detection signatures and examples of event displays by RP detection. Candidate MEI events were formed as clusters of supporting fragments. A limitation specific to RP detection arises from annotated elements within a characteristic read pair fragment length of candidate MEI. Read pairs spanning from a uniquely mapped anchor into an annotated mobile element with a fragment length consistent with the given library fragment length distribution are characteristic of the reference allele and are not evidence for non-reference MEI.

FIG. 9 shows a prior art RP signature for of non-reference MEI detection. The RP signature consists of Illumina read pairs spanning into the element from each side of the insertion. The RP event display shows a heterozygous Alu insertion allele on chromosome 22 from a pilot dataset. Fragment mapping quality is shown on the vertical scale. Horizontal lines show read pairs uniquely mapped at both ends with a mapped fragment length consistent with the sequence library; the short lines at the outer ends of the arc-shaped lines are read pairs spanning into an Alu sequence from the 5' and 3' ends. The central vertical line is the position of the insertion. Thick lines near the top show annotated Alu positions. Thus, FIG. 8 illustrates a clusters of paired-end reads for which a portion of reads map to the same part of the genome for the RP case. Clusters may also be found in the SR case or in other contexts.

For each cluster, methods include filtering the reads so that the mapped and unmapped portions are at least a base pairs long, where a is a constant chosen beforehand (it might be reasonable to choose a=10) and sorting the unmapped portions according to their expected left-to-right (where 'leftness' corresponds to smaller indices and 'rightness' greater indices according to some indexing scheme) positions. This can be deduced from the read length, the insert size, and the length of the mapped portions.

As used herein, insert size is generally taken to refer to length of a nucleic acid molecule being sequenced. Thus an insert size may be, for example, 500 base pairs, with a read length of 100 base pairs. Then the distance between the reads is approximately 300 base pairs, so that if the mapped portion is greater than 100 base pairs, the expected starting position of the yet-to-be-mapped portion is (the starting position of the mapped portion+100+300+(the length of the mapped portion−100)), which equals (the starting position of the mapped portion+300+the length of the mapped portion). If the mapped portion is shorter than the sequence length, there figure to be two unmapped portions, one of which begins at (the starting position of the mapped portion+the length of the mapped portion) and the other of which begins at (the starting position of the mapped portion+100+300), which equals (the starting position of the mapped portion+400). It is recognized that in some instances in the literature, "insert size" is used to refer to the space between reads. However, method described herein are equally applicable regardless of how "insert size" is used by making the appropriate adjustments in language usage.

Methods further include, for each cluster taking the first ("first" according to the sorting procedure, that is) unmapped portion and consider it as a reference object. Although it is a string, take it to be a (flat) DAG. Call it R.

For each remaining unmapped read-portion, in sorted order: align that read-portion to R; create a DAG representing that alignment; and update R to be the DAG created in the preceding step.

The result is a raw local assembly—a DAG representing the region about which the original alignment process did not give information. Therefore, this process makes important improvements over the status quo. It will give accurate sequence information about indels and structural variants that existing tools do not resolve or altogether ignore. One can further refine this assembly DAG into haplotypes.

4. Applications to Haplotying

By haplotype we mean here set of nearby variants inherited (usually) together and able to be considered as a unit. A process of determining haplotypes in a sample can be used along with the process described above, and any related process whereby many reads (or alignments) are sequentially aligned to a reference object, which thereby accumulates information.

Note first that haplotypes can be represented as paths through a DAG. A process of determining relevant haplotypes is therefore expressible as a process of determining relevant paths through a DAG.

The invention provides systems and methods for determining relevant haplotypes from a sequence DAG. Methods include aligning reads to a DAG and tracking how many reads are consistent with each location within the DAG and defining the support of a node in the DAG as the number of reads consistent with it. By extension, the support of a path through the DAG is defined as the minimum of the support values of each of the nodes in that path.

Once support for each of a plurality of paths through the DAG has been determined according to a number of reads consistent with a location in that path that is consistent with fewer reads than any other location in that path, then a number of the paths meeting a pre-determined support criteria may be identified as describing relevant haplotypes.

In certain embodiments, the foregoing steps may include the following specific methodological steps. Let n be the number of paths with support greater than or equal to some constant chosen before the process (perhaps 3% of the number of reads divided by the number of samples from which the reads were drawn). Let k be two times the number of human genomes represented in the set from which the reads were drawn. If n is less than or equal to k, then each of the n paths is a "relevant" haplotype. (Throughout this discussion, "relevant" means "evidentially supported in the sample to such a degree that one can posit its existence in the source of the sample.") Otherwise, the k best-supported haplotypes are the relevant ones.

5. Systems of the Invention.

Figure 10:
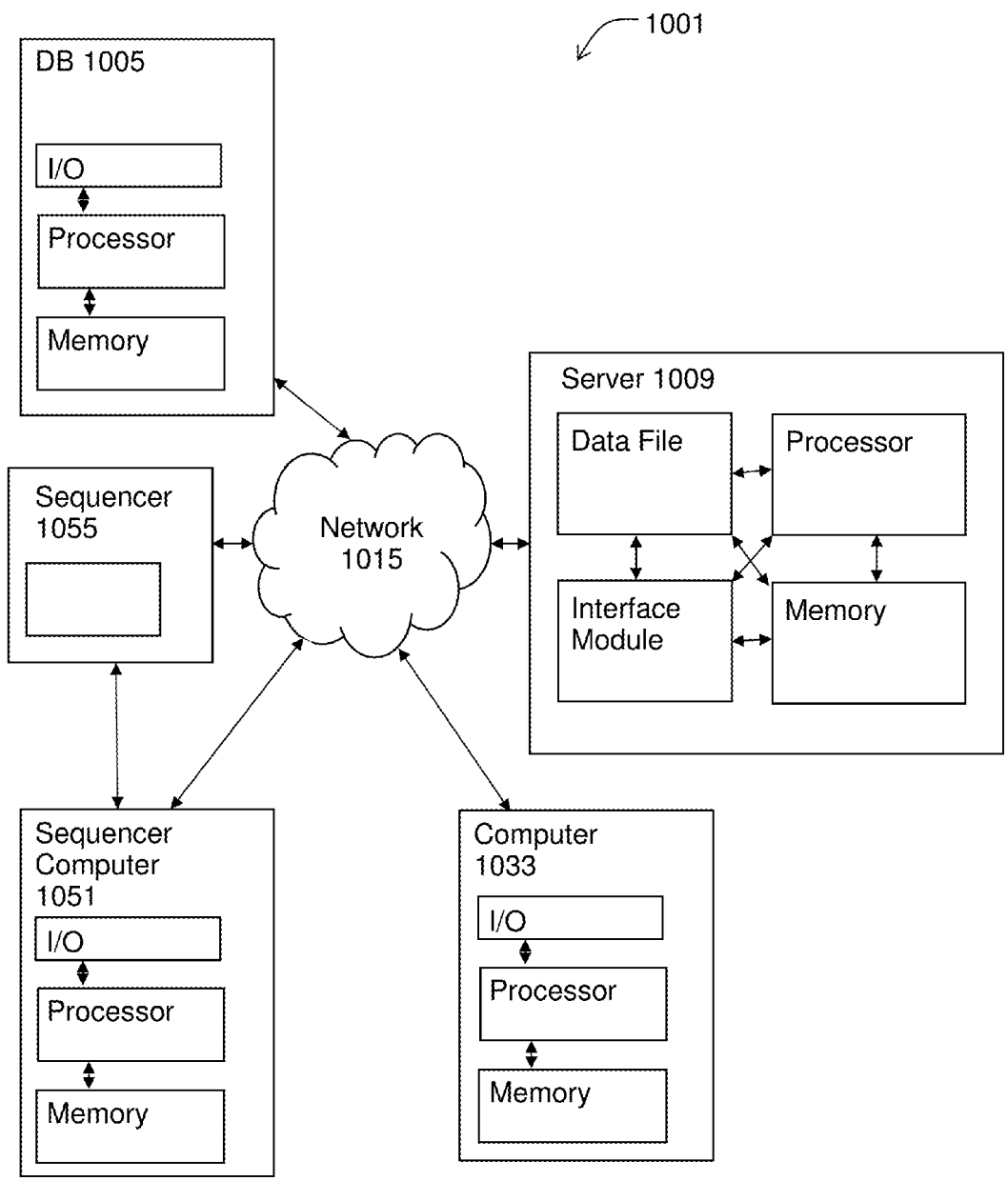
FIG. 10 illustrates a computer system according to embodiments of the invention.

FIG. 10 illustrates a computer system 1001 useful for implementing methodologies described herein. A system of the invention may include any one or any number of the components shown in FIG. 10. Generally, a system 1001 may include a computer 1033 and a server computer 1009 capable of communication with one another over network 1015. Additionally, data may optionally be obtained from a database 1005 (e.g., local or remote). In some embodiments, systems include an instrument 1055 for obtaining sequencing data, which may be coupled to a sequencer computer 1051 for initial processing of sequence reads.

In some embodiments, methods are performed by parallel processing and server 1009 includes a plurality of processors with a parallel architecture, i.e., a distributed network of processors and storage capable of comparing a first sequence DAG to a second sequence DAG. The system comprises a plurality of processors that simultaneously execute a plurality of comparisons between a plurality of reads and the reference sequence construct. While other hybrid configurations are possible, the main memory in a parallel computer is typically either shared between all processing elements in a single address space, or distributed, i.e., each processing element has its own local address space. (Distributed memory refers to the fact that the memory is logically distributed, but often implies that it is physically distributed as well.) Distributed shared memory and memory virtualization combine the two approaches, where the processing element has its own local memory and access to the memory on non-local processors. Accesses to local memory are typically faster than accesses to non-local memory.

Processor-processor and processor-memory communication can be implemented in hardware in several ways, including via shared (either multiported or multiplexed) memory, a crossbar switch, a shared bus or an interconnect network of a myriad of topologies including star, ring, tree, hypercube, fat hypercube (a hypercube with more than one processor at a node), or n-dimensional mesh.

Parallel computers based on interconnected networks incorporate routing to enable the passing of messages between nodes that are not directly connected. The medium used for communication between the processors is likely to be hierarchical in large multiprocessor machines. Such resources are commercially available for purchase for dedicated use, or these resources can be accessed via "the cloud," e.g., Amazon Cloud Computing.

One approach to parallelizing Smith-Waterman-type alignments is discussed in Altera, 2007, Implementation of the Smith-Waterman algorithm on reconfigurable supercomputing platform, White Paper ver 1.0 (18 pages), incorporated by reference.

A computer generally includes a processor coupled to a memory and an input-output (I/O) mechanism via a bus. Memory can include RAM or ROM and preferably includes at least one tangible, non-transitory medium storing instructions executable to cause the system to perform functions described herein. As one skilled in the art would recognize as necessary or best-suited for performance of the methods of the invention, systems of the invention include one or more processors (e.g., a central processing unit (CPU), a graphics processing unit (GPU), etc.), computer-readable storage devices (e.g., main memory, static memory, etc.), or combinations thereof which communicate with each other via a bus.

A processor may be any suitable processor known in the art, such as the processor sold under the trademark XEON E7 by Intel (Santa Clara, Calif.) or the processor sold under the trademark OPTERON 6200 by AMD (Sunnyvale, Calif.).

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for genomic analysis, the method comprising:
   representing a plurality of nucleic acids from a population of individuals as a reference directed acyclic graph (DAG) stored in a non-transitory memory, wherein the reference DAG includes nodes connected by edges in which at least one node includes a string of a plurality of nucleotide characters corresponding to a nucleotide sequence found within the plurality of nucleic acids;

obtaining a second DAG representing a second plurality of nucleic acids, the second plurality of nucleic acids comprising nucleic acids from one or more individuals;

determining, using a processor coupled to the non-transitory memory, an alignment between the second DAG and the reference DAG; and creating, from the alignment, an aligned DAG comprising an aligned combination of the reference DAG and the second DAG.

2. The method of claim 1, wherein each DAG comprises at least two alternative sequences per position at multiple positions in that DAG.

3. The method of claim 2, wherein determining the alignment comprises:

scoring sequence overlaps between the reference DAG and the second DAG, wherein greater overlap results in a higher score; and aligning portions of the second DAG to locations in the reference DAG such that the scores for the sequence overlaps are maximized.

4. The method of claim 1, wherein said alignment is an optimal alignment.

5. The method of claim 4, wherein said optimal alignment is a best-scoring DAG matrix alignment produced from a combination of said reference DAG and said second DAG.

6. The method of claim 5, wherein said best-scoring DAG alignment is determined by a mathematical construct representing the optimal path through a matrix of similarity scores in said combination.

7. The method of claim 1, wherein the second DAG is obtained from sequence reads from a sample from a subject.

8. The method of claim 7, wherein the reference DAG comprises a plurality of alleles associated with a disease.

9. The method of claim 7, wherein homozygous loci in the sample are represented using a single node in the second DAG and at least one heterozygous loci in the sample is represented using a plurality of different nodes in the second DAG.

10. The method of claim 1, wherein the steps are performed using a computer system comprising the processor coupled to the non-transitory memory having the reference DAG stored therein and further wherein the alignment is stored as a final DAG in the non-transitory memory.

11. The method of claim 1, wherein a DAG is stored as a computer file comprising:

nodes, each node comprising a character string and a label, and edges, each edge comprising a pair of labels.

12. The method of claim 1, wherein a DAG is stored as a computer file comprising:

nodes, each node comprising one or more characters representing nucleotides, and edges, each edge representing a connection between a pair of the nodes.

13. The method of claim 1, wherein at least one path through the reference DAG represents a sequence of a human chromosome.

14. The method of claim 13, wherein at least one path through the second DAG represents an alternative sequence of the human chromosome.

15. The method of claim 1, wherein the second DAG represents a transcriptome from an organism and the reference DAG represents one or more genomes from organisms of a same species as the organism.

16. The method of claim 1, wherein finding an optimally-scoring alignment between the second DAG and the reference DAG comprises:

calculating each of a plurality of values for entries in a matrix of similarities between the reference DAG and the second DAG based on a highest-valued neighboring entry and associating each calculated value with the highest-valued neighboring entry upon which the calculation of that calculated value was based; and identifying a path through the matrix that originates at the entry with the highest calculated value and traces sequentially through each associated neighboring entry until a zero entry is met, wherein the identified path indicates the optimally-scoring alignment.

17. The method of claim 1, wherein:

the reference DAG comprises a plurality of binary alignment map (BAM) entries that have been mapped to a first genomic reference; and the second DAG comprises a second plurality of BAM entries that have been mapped to a second genomic reference.

18. The method of claim 1, further comprising comparing genetic features between the population and the one or more individuals using the aligned DAG.

19. The method of claim 1, further comprising aligning a set of sequence reads to the aligned DAG.

* * * * *

SEQUENCE LISTING

```
<160> NUMBER OF SEQ ID NOS: 4

<210> SEQ ID NO 1
<211> LENGTH: 11
<212> TYPE: DNA
<213> ORGANISM: Homo sapiens

<400> SEQUENCE: 1
ttggatatgg g                                                    11

<210> SEQ ID NO 2
<211> LENGTH: 17
<212> TYPE: DNA
<213> ORGANISM: Homo sapiens

<400> SEQUENCE: 2
ttggatcgaa ttatggg                                              17

<210> SEQ ID NO 3
<211> LENGTH: 33
<212> TYPE: DNA
<213> ORGANISM: Homo sapiens

<400> SEQUENCE: 3
gattacacat gattacatga ctgaccattc cat                            33

<210> SEQ ID NO 4
<211> LENGTH: 36
<212> TYPE: DNA
<213> ORGANISM: Homo sapiens

<400> SEQUENCE: 4
gagtacagat tacatgactg acggagcatt acatct                         36
```